(12) United States Patent
Griessmann et al.

(10) Patent No.: US 12,076,471 B2
(45) Date of Patent: Sep. 3, 2024

(54) METHOD OF LOADING A MEDICAL DEVICE

(71) Applicant: FRESENIUS MEDICAL CARE DEUTSCHLAND GMBH, Bad Homburg (DE)

(72) Inventors: Erik Griessmann, Schweinfurt (DE); Klaus Wolf, Arnstein (DE); Peter Wabel, Darmstadt (DE); Bernd Mohr, Darmstadt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 806 days.

(21) Appl. No.: 16/319,600

(22) PCT Filed: Jul. 20, 2017

(86) PCT No.: PCT/EP2017/000886
§ 371 (c)(1),
(2) Date: Jan. 22, 2019

(87) PCT Pub. No.: WO2018/015019
PCT Pub. Date: Jan. 25, 2018

(65) Prior Publication Data
US 2020/0215249 A1    Jul. 9, 2020

(30) Foreign Application Priority Data

Jul. 20, 2016 (DE) .................... 10 2016 008 868.0

(51) Int. Cl.
*A61M 1/16* (2006.01)
*A61M 1/28* (2006.01)

(52) U.S. Cl.
CPC ............ *A61M 1/28* (2013.01); *A61M 1/1607* (2014.02); *A61M 1/1668* (2014.02);
(Continued)

(58) Field of Classification Search
CPC .... A61M 1/14; A61M 1/1607; A61M 1/1668; A61M 1/28; A61M 2205/14;
(Continued)

(56) References Cited

U.S. PATENT DOCUMENTS

2010/0315231 A1    12/2010   Rada
2011/0160649 A1*   6/2011    Pan .................... A61M 1/1643
                                                              177/1
(Continued)

FOREIGN PATENT DOCUMENTS

CN         103476486       12/2013
DE         102015010467    2/2017

*Primary Examiner* — Dirk R Bass
(74) *Attorney, Agent, or Firm* — Jacobson Holman PLLC

(57) ABSTRACT

The invention relates to a method of loading a medical device, in particular to a dialysis device, and preferably a peritoneal dialysis device, which comprises a device control and a user interface, wherein at least one fluid-filled container is connected to a corresponding interface of the device, wherein at least one property of the container is checked by the device before or during its connection and the measured value is compared with least one desired value stored in the device control.

2 Claims, 2 Drawing Sheets

Figure 1:
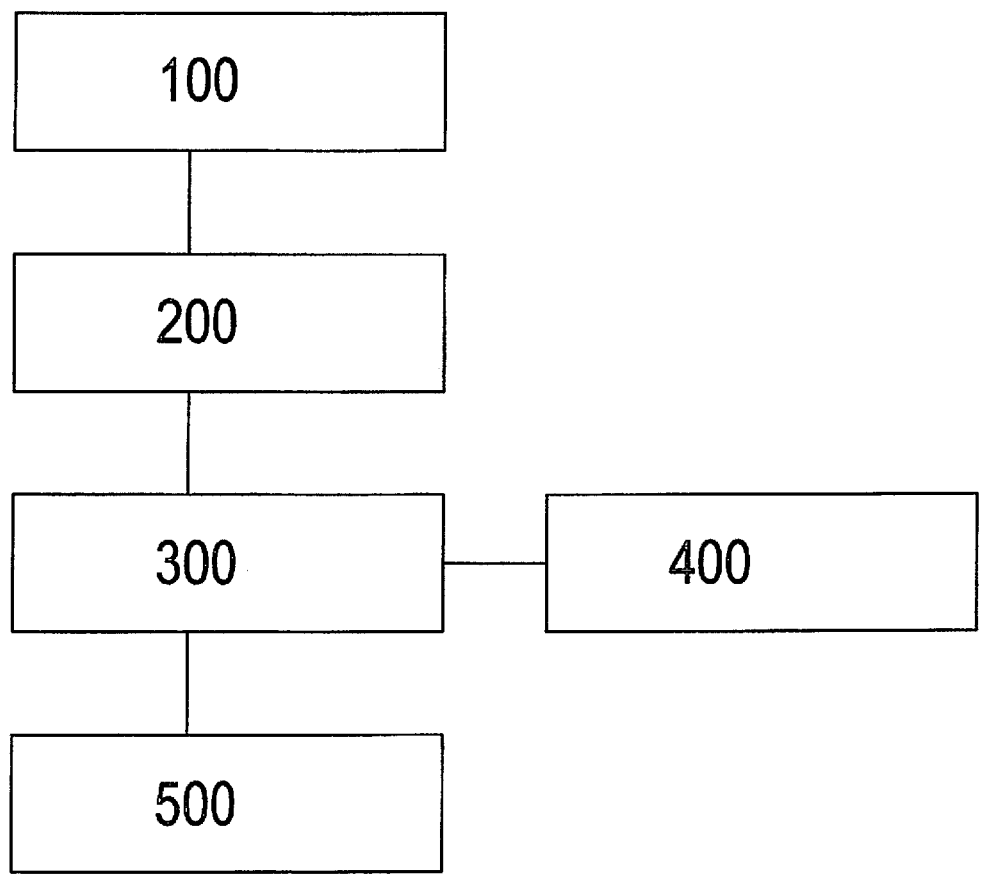

(52) U.S. Cl.
CPC ..... *A61M 2205/14* (2013.01); *A61M 2205/27* (2013.01); *A61M 2205/3393* (2013.01); *A61M 2205/502* (2013.01); *A61M 2205/6018* (2013.01)

(58) Field of Classification Search
CPC ...... A61M 2205/27; A61M 2205/3393; A61M 2205/502; A61M 2205/6018
See application file for complete search history.

(56) References Cited

U.S. PATENT DOCUMENTS

2011/0315611 A1   12/2011  Fulkerson et al.
2016/0022893 A1    1/2016  O'Mahony

* cited by examiner

METHOD OF LOADING A MEDICAL DEVICE

The invention relates to a method of loading a medical device, in particular a dialysis device, and preferably a peritoneal dialysis device, and to a medical device, in particular a dialysis device, such as a peritoneal dialysis device, for carrying out such a method.

Before carrying out a peritoneal dialysis treatment, the patient himself first has to connect to the peritoneal dialysis device and also has to connect different fluid containers to the device in a sufficient quantity. Errors can occur on an improper handling, which is, however, to be avoided at all costs since the treatment may otherwise not be carried out.

It is the object of the invention to provide an improved method of carrying out and checking the equipping procedure of a dialysis treatment.

Against this background, the invention relates to a method of loading a medical device, e.g. a dialysis device, and preferably a peritoneal dialysis device, which comprises a device control and a user interface, wherein at least one fluid-filled container is connected to a corresponding interface of the device, wherein at least one property of the at least one container is checked by the device before or during its connection and the measured value is compared with least one desired value range stored in the device control.

References to dialysis devices or to peritoneal dialysis devices made in the following generally also apply accordingly to medical devices.

In this respect, the containers placed on during the equipping phase are checked with respect to the volumes contained and/or are checked for plausibility against the individual patient therapy prescription. This in particular contributes to improved patient safety in the home dialysis area since possible incorrect loads or incorrect connections can be recognized by the patient on the basis of the plausibility check and since the proposed method also simultaneously comprises a user guidance in an embodiment.

The container is weighed before or during its connection in an embodiment. The checked property of the container in this embodiment is therefore the weight of the container which is compared with at least one desired value for the weight stored in the device.

In an embodiment, it is shown on the user interface whether the measured value lies within the desired value range or within predefined tolerance limits.

Alternatively, this can also be done via a different indicator than the weight such as via the volume or via the type of solution, etc.

In an embodiment, a connection of the container and/or subsequent steps are blocked by the device control when the measured value does not lie in the desired value range or within predefined tolerance limits.

Alternatively or additionally, a corresponding message can be output to the user.

In an embodiment, a plurality of fluid-filled containers are sequentially connected to corresponding interfaces of the device and one and, preferably, the same property is checked for all containers before or during its connection and the measured values are respectively compared with at least one desired value range stored in the device control. Provision can be made, for example, that a plurality of containers are placed sequentially onto the same scales and the respective weight difference is measured when a new container is added.

Instead of a plurality of containers, however, solution volumes can also be prescribed which have to be satisfied for a bag combination. If, e.g. for a therapy, e.g. 10,000 ml are prescribed, 2×5,000 ml or 2×6,000 ml can be used, for example, to fill the prescription. This is in particular relevant to the case that one solution type is present in different packaging sizes.

The containers can be bags, for example.

In an embodiment, the desired value range is fixed by the device control on the basis of stored values for respective properties of known containers and/or on the basis of a stored medical prescription.

Provision is made in an embodiment that the containers are connected at their measurement position. For example, the measurement is carried out at a heating and weighing pan of the dialysis device in which the connected containers are also located during a subsequent treatment.

Alternatively, the drain pan can also be provided as the measurement position since the weight of the drain pan is likewise detected. If too high a weight is recognized in this respect, a message can be given that the drain bag or drain container is/are full and/or should be emptied.

A function test (e.g. calibration) of the weighing system can also be carried out using the proposed method and/or a possible malfunction can be recognized.

Against the initially named background, the invention furthermore relates to a medical device, in particular to a dialysis device, and preferably to a peritoneal dialysis device, having a device control, a user interface and an interface for connecting at least one or more fluid-filled containers, wherein the device has a measuring unit for checking at least one property of the container, and wherein the device control is configured to carry out a method in accordance with any one of the preceding claims.

In an embodiment, the measuring unit is a scale.

In an embodiment, a common measuring unit is present for all the containers. The measurement position can correspond to the final connection space of the containers.

The measuring unit can, for example, be a heating pan, a drain pan and a weighing pan of the dialysis device.

In an embodiment, the device control is furthermore configured to check a property of a further container, which is connected to the device during or at the end of a treatment, before or during its connection and to compare the measured value with at least one desired value stored in the device control. The inventive principle in this embodiment can therefore not only be used in the preparation phase, but additionally also when the connection of a further container is necessary during or at the end of a treatment.

In an embodiment, the invention therefore relates to the sequential loading of the heating and/or weighing pan of a dialysis device, in particular of a peritoneal dialysis device, with containers filled with dialysis fluid and to a plausibility check of the containers placed on.

In a further embodiment, the heating can also be arranged independently of the device.

Figure 2:
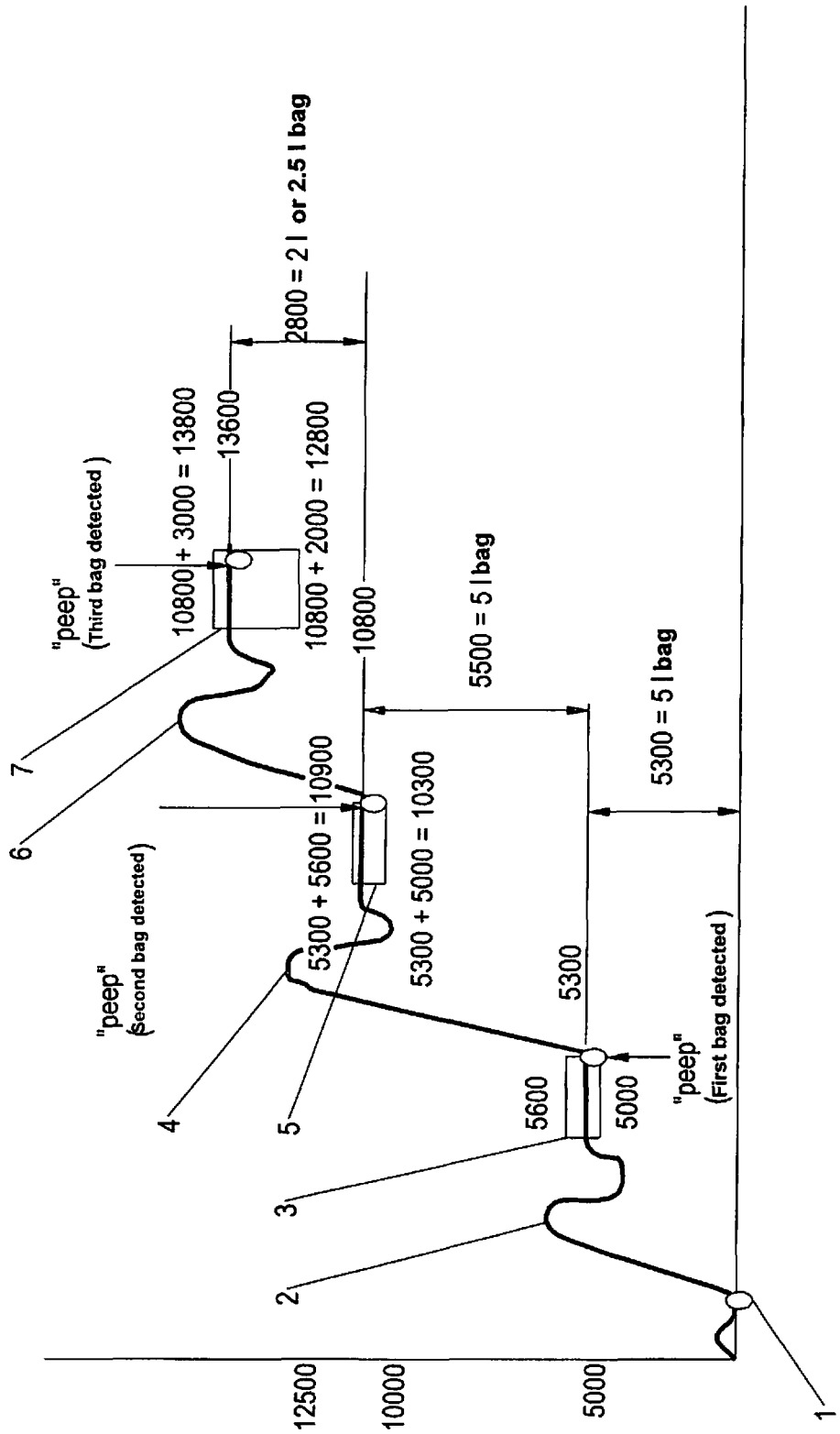

Further details and advantages of the invention result from the embodiment described in the following and from the Figures. There are shown in the Figures:

FIG. 1: a schematic representation of a method routine in accordance with the invention; and FIG. 2: a schematic representation of the progression of the measured values for the weight of the connected bags.

A dialysis device in accordance with the invention in accordance with the embodiment is equipped with a heating and/or weighing pan and has a user guidance which guides the user/patient through the preparation phase of his treatment and which can check the containers placed on with respect to their plausibility for the intended treatment in an internal process.

FIG. 1 shows a schematic representation of a possible method for loading a dialysis device in accordance with the embodiment.

In this respect, the user is prompted by the user interface in a first step 100 to check that no articles, in particular containers, are located on the heating and/or weighing pan and in the drain pan.

The weighing system fixes the state of the unloaded heating and/or weighing pan and of the drain pan as the zero point. In this respect, a tolerance band can be provided for the zero point in the range between +/−500 to +/−20 g, preferably in the range from +/−300 to +/−100 g, and particularly preferably from +/−200 to +/−150 g.

Subsequent to this, the user or patient is prompted via the user interface in a further step 200 to place the first container onto the heating and/or weighing pan. Foil bags are preferably used as the containers.

The device recognizes the weight of the bag and compares it with a list of possible bag volumes stored in the device. A stabilization phase, which can last 2 seconds from the placing on of the bag, for example, improves the measurement accuracy. Since the material of the container and an overfilling with dialysis fluid caused by production can be included in the weight measurement, a tolerance range is also provided here in dependence on the provided bag volumes. Examples for suitable tolerance limits dependent on bag size are named in Table 1 below.

TABLE 1

| Bag volume | Lower tolerance limit | Upper tolerance limit |
| --- | --- | --- |
| 2,000 ml | 2,000 g | 2,500 g |
| 2,500 ml | 2,500 g | 3,000 g |
| 5,000 ml | 5,000 g | 5,600 g |
| 6,000 ml | 6,000 g | 6,600 g |

At the same time, the device checks whether the recognized bag volume also corresponds to the corresponding therapy prescription of the patient. If the device recognizes both criteria (container with correct fluid volume was placed on and agrees with prescription) as satisfied, the patient or user is prompted to place the next container on. The plausibility check for the second bag and for further bags is likewise carried out as described above.

FIG. 2 shows a schematic representation of the development of the weight signal when a plurality of bags are placed on. The zero point is marked by reference numeral 1. The first bag is then placed on. After a fluctuating measured signal in a stabilization phase 2, a weight of 5,300 g is recognized during a measurement phase 3. This weight is associated with a bag volume of 5,000 ml and is classified as plausible with reference to the stored therapy prescription. 5,300 g is then assumed as the new reference point and a second bag is placed on. After a fluctuating measured signal in a second stabilization phase 4, a weight of 5,500 g is recognized during a second measurement phase 5. This weight is also associated with a bag volume of 5,000 ml and is classified as consistent with reference to the stored therapy prescription. The current total weight of 10,800 g is now assumed as the new reference point and a third bag is placed on. After a fluctuating measured signal in a third stabilization phase 6, a weight of 2,800 g is recognized during a third measurement phase 7. This weight can correspond with a bag volume of 2,000 ml or 2,500 ml, with one of the two volumes agreeing with the stored therapy prescription and therefore being recognized as consistent overall.

If e.g. only two bags are provided for a prescription, the total weight has been reached after the loading of the second bag and the sequence is automatically ended. The user is then not prompted to place a further bag on.

In accordance with a further step 300, a plausibility check can take place in which a query is made whether a dialysis solution exists which corresponds with the bag combination used. A query can further be made whether a maximum volume of a total of 14,500 ml has not been exceeded and/or whether a maximum number of different bags of 3 has not been exceeded.

A solution type having only one specific concentration can be prescribed, for example, which is only available in a bag size corresponding to the solution type. If a different bag size or bag volume is placed on, it can be recognized therefrom that the correct solution type or the correct solution bag has not been placed on. Fewer than the existing treatment positions can also be used for one prescription.

If the device measures a weight which does not correspond to any plausible predefined bag volume or is not in agreement with the therapy prescription, an error message is output in a step 400 which prompts the user or patient to place the correct container on. The equipping of the device can only be continued after the automatic check of the error remedy.

On a successful loading, the therapy is released in a step 500.

Optionally, a last filling of the patient with dialyzate can be provided at the end of the treatment in the therapy prescription. The prescription provides the placing on of a last bag as a further step for this purpose. The device also recognizes here whether the user or patient has placed on this last bag in accordance with the prescription. In this case, the routine is changed—optionally on a graphical user interface—and a further terminal is switched in.

The device likewise correspondingly recognizes when an additional bag has been placed on which is not planned according to the prescription and prompts the user or patient to remove it from the heating and/or weighing pan.

If it can be ensured by the user or patient on a false alarm that all the bags have been placed on correctly and also agree with the prescription, but if the false alarm is still being displayed, this provides an indication that it may be a defect of the weighing system.

There is a further advantage that all the dialyzate bags used for the treatment can be checked for their plausibility with respect to the bag volumes placed on and with respect to the prescription using this method and thus provide increased therapy safety.

The method furthermore allows a user guidance which guides the user or patient step by step through the equipping process and thus represents a substantial contribution to patient safety.

Since holding elements in the form of holding hoops and/or side walls which can be plugged on have to be attached both to the heating and/or weighing pan and to the drain pan to avoid the containers slipping off, it is also possible to monitor whether these safety-relevant parts have been installed via the determined weight in an embodiment of the invention. This requires that the weights for the fully installed heating pan and drain pan are stored in the device.

It is also possible in an embodiment to carry out an identification of the solution type in a simple manner by means of a controlled overfilling of the dialyzate bags. An overfilling due to production can be fixed via the nominal volumes of the bags for each individual solution type for this purpose. The weight, which is thus specific to each solution type, can likewise be stored in a table for the plausibility comparison. A tolerance band for each solution type can likewise also be provided here.

At the same time, the overfill volume can be determined by means of the weighing system and can also be used as a therapy volume in the treatment. This produces considerable advantages since the complete volume in the bags, including the overfill volume, can be used for the therapy.

Furthermore, the filling weight due to production can be stored in the device for every single solution type and can, for example, be linked with a production date, lot number or batch number, which can be used for a closer specification of the dialysis fluid. It is also conceivable that solution-specific or production-specific data can be manually input or can be transmitted to the device by means of a smartphone, e.g. by reading a QR code or barcode or by near field communication or by cloud.

Incorrect/defective bags can thus also be recognized. For example, bags which have been recognized as expired due to the production date or bags which do not correspond to the specified filling weight since they have been stored at too high a temperature, for example, and thus have too low a weight.

The invention claimed is:

1. A method of loading a peritoneal dialysis device, which has a device control, a weighing scale, and a user interface, wherein at least one fluid-filled container is connected to a corresponding interface of the device, characterized in that
   a plurality of the fluid-filled containers are placed sequentially onto the scale, the weight is measured as each container is placed on the scale, and each measured value is compared with (i) a desired value having predefined tolerance limits stored in the device control and (ii) a therapy prescription stored in the device control,
   it is displayed at the user interface whether the measured value corresponds to (i) the desired value or lies within the predefined tolerance limits and (ii) the therapy prescription,
   a plausibility check is performed by the medical device with respect to the volumes of the containers placed on and with respect to the therapy prescription, wherein in the plausibility check a query is made whether a dialysis solution exists which corresponds with the container combination used,
   as the plurality of fluid filled containers are weighed, each weight of an individual bag is used as a new reference point and total accumulated weight of the plurality of fluid filled containers is determined, and the determined value is compared with the therapy prescription stored in the device control,
   it is displayed at the user interface whether the determined value corresponds to the therapy prescription,
   a further plausibility check is performed by the medical device with respect to the total volume of the containers placed on and with respect to the therapy prescription, and
   a connection of the containers and/or subsequent steps are blocked by the device control if either (a) the measured value (i) does not correspond to the desired value or does not lie within the predefined tolerance limits and/or (ii) does not correspond to the therapy prescription or (b) the determined value does not correspond to the therapy prescription.

2. A peritoneal dialysis device, comprising a device control, a user interface and an interface for connecting fluid-filled containers, characterized in that
   the device has a scale for weighing the containers; and in that the device control is configured to carry out a method in accordance with claim 1.

* * * * *